US012797028B2

(12) United States Patent
Liu

(10) Patent No.: US 12,797,028 B2
(45) Date of Patent: Nov. 17, 2026

(54) METHOD FOR REMOVING ARTIFACT IN IMAGE, ELECTRONIC DEVICE, AND STORAGE MEDIUM

(71) Applicant: SHANGHAI UNITED IMAGING HEALTHCARE CO., LTD., Shanghai (CN)

(72) Inventor: Yan-Yan Liu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 406 days.

(21) Appl. No.: 18/383,910

(22) Filed: Oct. 26, 2023

(65) Prior Publication Data

US 2024/0138798 A1 May 2, 2024

(30) Foreign Application Priority Data

Oct. 26, 2022 (CN) ......................... 202211319983.6

(51) Int. Cl.
*A61B 6/00* (2024.01)
*A61B 6/03* (2006.01)
*G06T 12/10* (2026.01)

(52) U.S. Cl.
CPC ............ *A61B 6/5282* (2013.01); *A61B 6/032* (2013.01); *A61B 6/037* (2013.01); *A61B 6/483* (2013.01); *G06T 12/10* (2026.01)

(58) Field of Classification Search
None
See application file for complete search history.

(56) References Cited

U.S. PATENT DOCUMENTS 5,949,842 A * 9/1999 Schafer .................. G01V 5/226 378/57
6,876,718 B2 * 4/2005 Tang ...................... G21K 1/025 378/7

(Continued)

FOREIGN PATENT DOCUMENTS

CN 103135121 A 6/2013
CN 106264722 A 1/2017

(Continued)

OTHER PUBLICATIONS

Zhao, Qingjun, "Types of CT Image Artifacts and Correction Methods", Medical Devices Information, No. 5, Oct. 30, 1998, (2 pages).

(Continued)

*Primary Examiner* — Uzma Alam
*Assistant Examiner* — Djura Malevic

(57) ABSTRACT

The present disclosure relates to a method for removing an artifact in an image, an electronic device, and a storage medium. The method includes obtaining original scan data of a target object collected by a detector during a first imaging scanning, and performing an artifact correction on the original scan data with a scattering reference signal. The original scan data includes a scattering signal. The scattering reference signal is obtained based on energy data of the detector obtained under a condition that no slit is applied and energy data of the detector obtained under a condition that a slit is applied during a second imaging scanning.

19 Claims, 7 Drawing Sheets

(56) References Cited

U.S. PATENT DOCUMENTS

| | | | | |
|---|---|---|---|---|
| 7,200,201 | B2 * | 4/2007 | Unger | A61B 6/06<br>378/150 |
| 2020/0279410 | A1 * | 9/2020 | Lee | G06T 7/70 |
| 2021/0131980 | A1 * | 5/2021 | Suppes | G21K 1/02 |

FOREIGN PATENT DOCUMENTS

| | | | | | |
|---|---|---|---|---|---|
| CN | 103135121 | B | | 4/2017 | |
| CN | 109801343 | A | | 5/2019 | |
| CN | 113177991 | A | | 7/2021 | |
| EP | 1151322 | B1 | * | 8/2006 | G01T 1/1648 |
| EP | 3982115 | A1 | | 4/2022 | |
| WO | 2006070316 | A1 | | 7/2006 | |
| WO | WO-2007028692 | A1 | * | 3/2007 | A61B 6/583 |

OTHER PUBLICATIONS

Yuan Lulu etal., "A deep learning-based ring artifact correction method for X-ray CT", Radiation Detection Technology and Methods, vol. 5, Nov. 23, 2021 (11 pages).

Office Action of CN2022113199836.

* cited by examiner

METHOD FOR REMOVING ARTIFACT IN IMAGE, ELECTRONIC DEVICE, AND STORAGE MEDIUM

CROSS-REFERENCE TO RELATED APPLICATIONS

The present application claims priority to Chinese patent application No. 202211319983.6, entitled "METHOD FOR REMOVING ARTIFACT IN IMAGE, ELECTRONIC DEVICE, AND STORAGE MEDIUM", filed on Oct. 26, 2022, the entire content of which is incorporated herein by reference.

TECHNICAL FIELD

The present disclosure relates to the field of computed tomography imaging technology, particularly to a method for removing an artifact in an image, an electronic device, and a storage medium.

BACKGROUND

Computed tomography (CT) imaging devices are used to construct images through transmission lines (beams). These transmission lines are generated by X-rays. However, after passing through the human body or an object, X-rays generate both transmission and scattering lines. The scattering lines are disadvantageous to the reconstructed image and thus need to be removed. A detector is the most important part of the device as it transforms the X-rays incident on it into electrical signals. The detector guides the X-ray beams emitted by the X-ray tube to the corresponding pixels on detector modules. The detector is formed by combining the detector modules.

SUMMARY

One aspect of the present invention provides a method for removing an artifact in an image. The method includes obtaining original scan data of a target object collected by a detector during a first image scanning, and performing an artifact correction on the original scan data with a scattering reference signal. The original scan data contains a scattering signal. The scattering reference signal is obtained based on energy data of the detector obtained under a condition that no slit is applied and energy data of the detector obtained under a condition that a slit is applied during a second imaging scanning.

In some embodiments, the energy data of the detector obtained under the condition that no slit is applied includes an energy intensity value of the detector obtained under a condition that no phantom is present and no slit is applied, and an energy intensity value of the detector obtained under a condition that a phantom is present and no slit is applied. The energy data of the detector obtained under the condition that the slit is applied includes an energy intensity value of the detector obtained under the condition that no phantom is present and the slit is applied, and an energy intensity value of the detector obtained under a condition that the phantom is present and the slit is applied. The phantom is configured to simulate the target object during a second imaging scanning. The first imaging scanning and the second imaging scanning are each a CT scanning, a PET-CT scanning, or an enhancement CT scanning.

In some embodiments, the performing the artifact correction on the original scan data with the scattering reference signal includes performing a scatter intensity estimation on the original scan data to obtain an original scattering signal, inputting the original scattering signal into a first fitting function to obtain the scattering signal, where coefficients of the first fitting function are determined based on the scattering reference signal, removing the scattering signal from the original scan data to obtain artifact-corrected original scan data, and reconstructing an image based on the artifact-corrected original scan data.

In some embodiments, the determination of the coefficients of first fitting function includes obtaining the scattering reference signal includes a first detector response under the condition that no phantom is present and no slit is applied, a second detector response under the condition that the phantom is present and no slit is applied, a third detector response under the condition that no phantom is present and the slit is applied, and a fourth detector response under the condition that the phantom is present and the slit is applied; and determining the coefficients of first fitting function based on the first detector response, the second detector response, the third detector response, and the fourth detector response.

In some embodiments, the calculating normalized intensities of the fourth detector responses corresponding to different slit positions, the normalized intensity of the fourth detector response being equal to a ratio of the fourth detector response to the third detector response; concatenating the normalized intensities corresponding to different slit positions to form a normalized intensity for all pixels of the detector; calculating a normalized intensity of the second detector response, the normalized intensity of the second detector response being equal to a ratio of the second detector response to the first detector response; obtaining a scatter intensity by removing normalized intensity for all pixels of the detector from the normalized intensity of the second detector response; smoothing the scatter intensity to obtain a smoothed scatter intensity; and performing fitting with the smoothed scatter intensity as the x-coordinate and the scatter intensity as the y-coordinate to obtain the coefficients of the first fitting function.

In some embodiments, the performing the scatter intensity estimation on the original scan data to obtain the original scattering signal includes analyzing the original scan data using an algorithm, model, or neural network to obtain the original scattering signal.

In some embodiments, the method further includes performing an artifact correction on the original scan data containing a projection signal with a projection reference signal to obtain projection-corrected original scan data. The projection reference signal is obtained based on an energy intensity value of the detector obtained under a condition that no phantom is present and the slit is applied and an energy intensity value of the detector obtained under a condition that the phantom is present and the slit is applied during CT scanning.

In some embodiments, the performing the artifact correction on the original scan data containing the projection signal with the projection reference signal includes transforming the original scan data into projection data, and inputting the projection data into a second fitting function to obtain the corrected projection data. The coefficients of the second fitting function are determined based on the projection reference signal.

In some embodiments, the determination of the coefficients of the second fitting function includes obtaining the projection reference signal including a third detector response under a condition that no phantom is present and a slit is applied, and a fourth detector response under a condition that the phantom is present and the slit is applied, and determining the coefficients of the second fitting function based on the third detector response and the fourth detector response.

In some embodiments, the determining the coefficients of the second fitting function based on the third detector response and the fourth detector response includes: calculating projection values corresponding to different slit positions by performing a log operation on a ratio of the third detector response to the fourth detector response; concatenating the projection values corresponding to the different slit positions to form a projection value for all pixels of the detector; smoothing the projection value for all pixels of the detector to obtain a smoothed projection value; and performing fitting with the smoothed projection value as the y-coordinate and the projection value as the x-coordinate to obtain the coefficients of the second fitting function.

In some embodiments, the performing the artifact correction on the original scan data with the scattering reference signal includes performing the artifact correction on the projection-corrected original scan data with the scattering reference signal.

In some embodiments, before performing the artifact correction on the original scan data containing the projection signal with the projection reference signal, the method further includes performing an air correction on the original scan data to obtain air-corrected original scan data.

In some embodiments, the method further includes: analyzing the original scan data using an algorithm, model, or neural network to obtain original scattering signal, removing the original scattering signal from the projection-corrected original scan data to obtain artifact-corrected original scan data, and reconstructing an image based on the artifact-corrected original scan data.

In some embodiments, the energy data of the detector obtained under the condition that the slit is applied includes energy data generated by the detector when a baffle with the slit is placed between the detector and a light source, and the energy data of the detector obtained under the condition that no slit is applied includes energy data generated by the detector when the baffle with the slit is removed.

Another aspect of the present disclosure provides a method for removing an artifact in an image. The method includes obtaining original scan data of a target object, the original scan data being collected by a detector during a first imaging scanning, the original scan data containing a projection reference signal; and performing an artifact correction on the original scan data with a projection reference signal to obtain projection-corrected original scan data, wherein the projection reference signal is obtained based on an energy intensity value of the detector obtained under a condition that no phantom is present and the slit is applied and an energy intensity value of the detector obtained under a condition that the phantom is present and the slit is applied during a second imaging scanning.

Another aspect of the present disclosure provides an electronic device. The electronic device includes a memory, a processor, and a computer program stored in the memory and executable by the processor. The processor, when executing the computer program, performs a method for removing an artifact in an image according to any one of the above-described embodiments.

Yet another aspect of the present disclosure provides a computer-readable storage medium. The computer-readable storage medium includes a computer program stored therein. The computer program, when executed by a processor, causes the processor to perform a method for removing an artifact in an image according to any one of the above-described embodiments.

The details of the various embodiments of the present disclosure will be illustrated with the accompanying drawings and description below, based on which, other features, problems to be solved, and beneficial effects of the disclosure will be readily understood by those skilled in the art.

DETAILED DESCRIPTION

Figure 1:
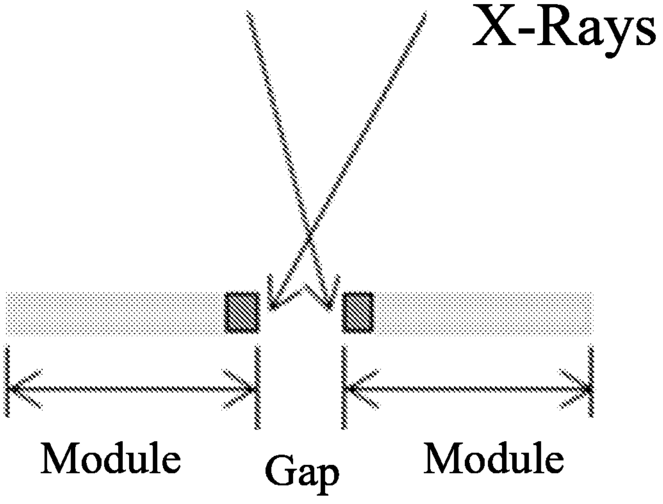
FIG. 1 is a schematic diagram illustrating the generation of artifacts by X-rays passing through a gap between detector modules.

According to the applicant's observation, due to inevitable gaps between detector modules as shown in FIG. 1, some X-rays scatter and enter the edge pixels (i.e., the dark squares in FIG. 1) when they pass through the gaps. The scattering of X-rays will cause the edge pixels of the detector to receive more X-ray signals than actual amounts. In the final reconstructed image, the edge pixels of the detector are prone to produce artifacts, affecting the quality of the final reconstructed image. To remove the artifacts, improvements are usually made on the hardware equipment. For example, a grid can be placed above the gap in FIG. 1 to reduce the scattering of X-ray signals. However, this method increases the complexity of the hardware and production costs and is unable to fundamentally solve the problem of artifacts in the images generated by CT devices.

Embodiments are provided to illustrate the present disclosure. It should be noted that the present disclosure is not limited to these embodiments.

Embodiment I

Figure 2:
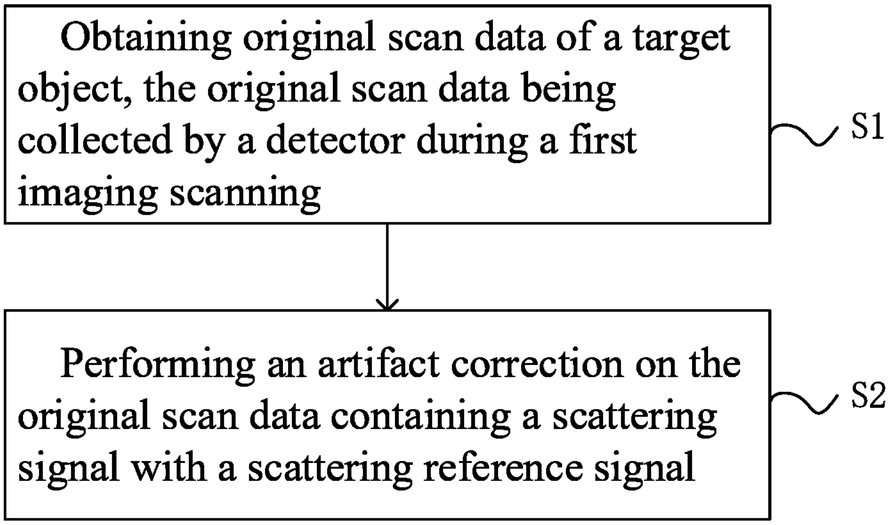
FIG. 2 shows a first flowchart of a method for removing an artifact in an image according to a first embodiment of the present disclosure.

This embodiment provides a method for removing an artifact in an image, which can be applied to images constructed by computed tomography devices such as CT devices, PET-CT (Positron Emission Computed Tomography) devices, or enhancement CT devices. Referring to FIG. 2, the method for removing an artifact in an image includes steps S1 and S2.

In step S1, original scan data of a target object is obtained. The original scan data being is collected by a detector during a first imaging scanning. For example, the original scan data of the target object is acquired from the detector during the first imaging scanning and used for imaging. Alternatively, the original scan data acquired from the detector during the first imaging scanning is stored first, and is then retrieved for imaging. The target object is a biological tissue. For example, the head of a person can be scanned by a CT or PET device, in which the head is the target object. The original scan data contains a scattering signal.

In some embodiments, the first imaging scanning is a CT scanning, a PET-CT scanning, or an enhancement CT scanning.

In step S2, an artifact correction is performed on the original scan data with a scattering reference signal.

The scatter reference signal is obtained during a second imaging scanning based on energy data of the detector obtained under a condition that no slit is applied and under a condition that a slit is applied. The energy data contains a scattering signal, a projection signal, and other energy data.

In some embodiments, the second imaging scanning is a CT scanning, a PET-CT scanning, or an enhancement CT scanning.

In the present application, "under a condition that no slit is applied" refers to that no slit is applied between the detector and a light source, and "under a condition a slit is applied" refers to that a slit is applied between the detector and the light source. These conditions are realized, for example, by placing or removing a baffle with a slit between the detector and the light source.

Figure 10:
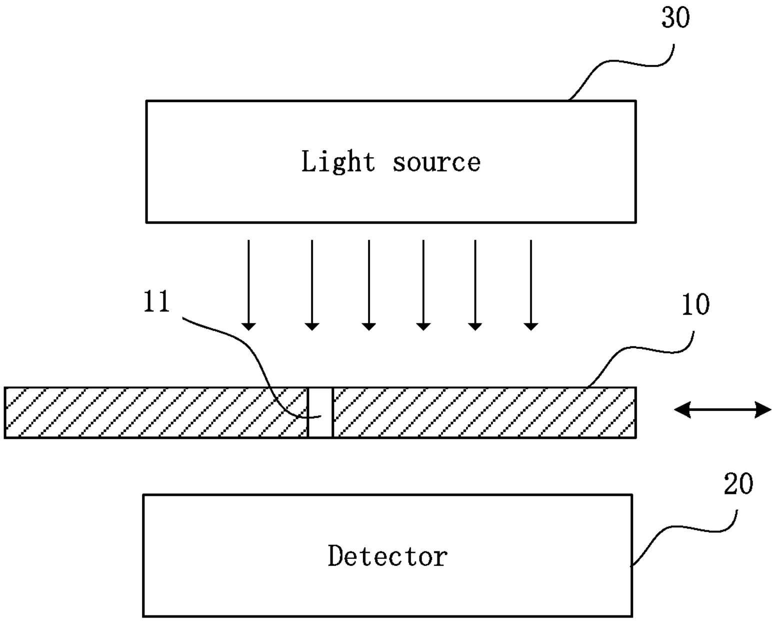
FIG. 10 and FIG. 11 are schematic diagrams of a scanning device, showing a slit of a baffle corresponding to different positions of a detector, respectively, according to an embodiment of the present disclosure.
Figure 11:
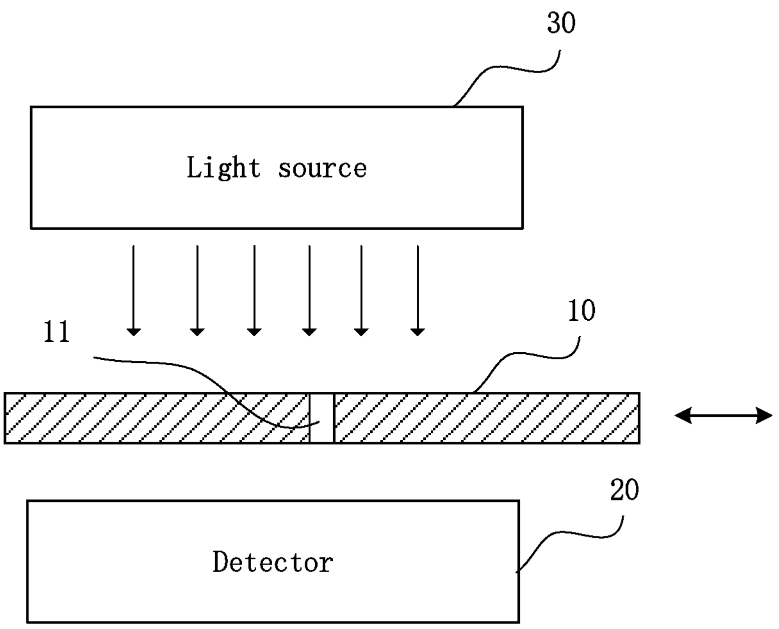

When obtaining the energy data of the detector under the condition that a slit is applied, regions of the detector other than the slit are blocked such that the amount of the scattering signals in the original scan data corresponding to the slit is less than a threshold. Referring to FIG. 10 and FIG. 11, in an embodiment, a baffle 10 with a single slit 11 is used. The slit 11 can be a narrow one with a preset width. The baffle 10 with the slit 11 is placed between a detector 20 and a light source 30, to receive a fixed amount of scattering signals of the original scan data. The baffle 10 is placed above the detector 20, and may be either in contact with the detector 20 or separated away from the detector 20. The width of the slit is determined based on the total amount of scattering signals in the original scan data and the threshold. For example, the slit allows light signals to pass through such that only 20 pixels (i.e., detector pixels used to receive X-rays and output response data) are irradiated. During an actual operation, the slit needs to be moved to different positions (as shown in FIG. 10 and FIG. 11) so that all detector pixels can be irradiated by X-rays to collect energy data for all the detector pixels under the condition that the slit is applied.

In some embodiments, the energy data of the detector obtained under the condition that no slit is applied includes an energy intensity value of the detector obtained under a condition that no phantom is present and no slit is applied, and an energy intensity value of the detector obtained under the condition that a phantom is present and no slit is applied.

The energy data of the detector obtained under the condition that the slit is applied includes an energy intensity value of the detector obtained under a condition that no phantom is present and the slit is applied, and an energy intensity value of the detector obtained under a condition that a phantom is present and a slit is applied.

The phantom is used to simulate the target object during CT scanning. The phantom can be made of materials such as Teflon or water, and the thickness of the phantom is greater than or equal to 3 millimeters to mimic the thickness of a human tissue.

In some embodiments, the baffle with the slit is placed between the phantom and the light source, in the presence of the phantom.

In some embodiments, multiple different phantoms are respectively used to collect the energy data of the detector under the condition that a slit is applied. Image reconstructions are performed based on the artifact-corrected original scan data to obtain an artifact-free medical image of the target object.

In some embodiments, the filtered back-projection (FBP) method is used to reconstruct an image based on the artifact-corrected original scan data, so as to obtain the artifact-free medical image of the target object.

In the present embodiment, the scatter reference signals obtained based on the energy data of the detector obtained under the condition that no slit is applied and the energy data of the detector obtained under the condition that a slit is applied are used to perform artifact correction on the original scan data containing the scattering signal, thereby removing, for example, ring artifacts in the medical images and achieving better imaging results.

Figure 3:
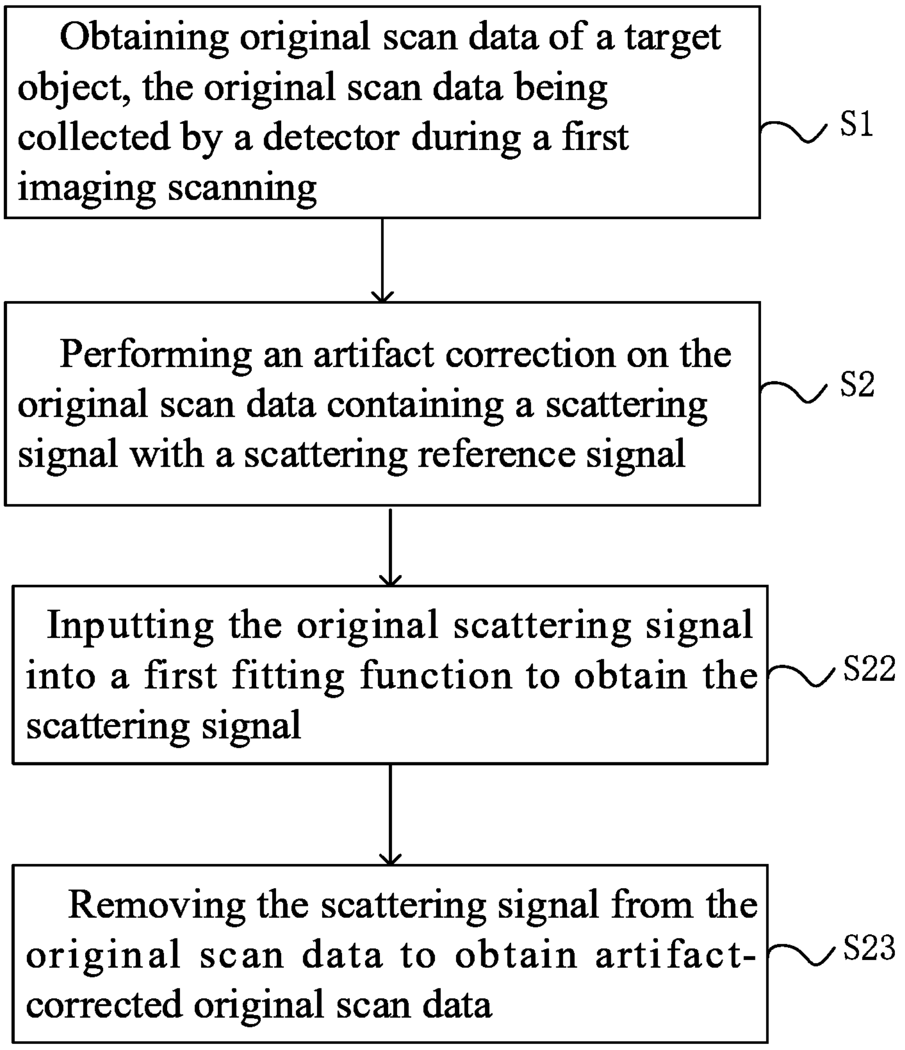
FIG. 3 shows a second flowchart of a method for removing an artifact in an image according to the first embodiment of the present disclosure.

In some embodiments, as shown in FIG. 3, step S2 includes steps S21-S23.

In step S21, a scatter intensity estimation is performed on the original scan data to obtain an original scattering signal.

The scatter intensity estimation includes analyzing the original scan data signal using algorithms, models, neural networks, etc., to obtain the original scattering signal from the original scan data. Methods for the scatter intensity estimation include convolution, Monte Carlo algorithms, deep learning, etc.

In step S22, the original scattering signal is input into a first fitting function to obtain the scattering signal, where coefficients of the first fitting function are determined based on the scattering reference signal.

The fitting involves using a fitting function to fit the original scattering signal to obtain an objective scattering signal. The scattering signal obtained after the fitting by the fitting function is closer to the actual scattering signal contained in the original scan data.

In some embodiments, the first fitting function includes an exponential function or a polynomial function.

In some embodiments, the determination of coefficients of the first fitting function includes:

obtaining a first detector response (e.g., $A_{empty}$) under the condition that no phantom is present and no slit is applied, a second detector response (e.g., $I_{empty}$) under the condition that the phantom is present and no slit is applied, a third detector response (e.g., $A_{spectra}$) under the condition that no phantom is present and the slit is applied, and a fourth detector response (e.g., $I_{spectra}$) under the condition that the phantom is present and the slit is applied; It can be understood that a detector response can be directly acquired from the detector, and based on the detector response, a corresponding energy data (e.g., an intensity value) can be determined.

calculating normalized intensity values corresponding to different slit positions using the following equation:

$$NI_{spectra}=I_{spectra}/A_{spectra};$$

concatenating the normalized intensity values corresponding to different slit positions to form a normalized intensity value (e.g., $NI_{spectra-all}$) for all pixels;

calculating a normalized intensity (e.g., $NI_{empty}$) of the second detector response (e.g., $I_{empty}$) using the following equation:

$$NI_{empty}=I_{empty}/A_{empty};$$

calculating the scatter intensity using the following equation:

$$I_{scatter}=NI_{empty}-NI_{spectra-all};$$

smoothing the scatter intensity obtained for each phantom thickness to obtain the smoothed scatter intensity (e.g., $I_{scatter-smooth}$), where smoothing methods include, for example, first-order exponential smoothing, second-order exponential smoothing, third-order exponential smoothing; and performing fitting with the scatter intensity (e.g., $I_{scatter}$) as the y-coordinate and the smoothed scatter intensity (e.g., $I_{scatter-smooth}$) as the x-coordinate to obtain the fitting coefficients of the first fitting function.

In this embodiment, the phantom can be made of materials such as Teflon or water. The thickness of the phantom should be greater than or equal to 3 millimeters to mimic the thickness of a human tissue.

In step S23, the scattering signal is removed from the original scan data to obtain artifact-corrected original scan data.

In this embodiment, the scattering signal in the original scan data is removed through the scatter intensity estimation and the fitting algorithm. This realizes artifact correction on the original scan data by removing the scatter signal from the original scan data, and simplifies the correction of artifacts, which reduces maintenance costs and improves imaging quality.

In some embodiments, the method for removing an artifact in an image also includes step S3.

In step S3, an artifact correction is performed on the original scan data containing a projection signal with a projection reference signal.

The projection reference signal is obtained based on the energy intensity value of the detector obtained under the condition that no phantom is present and the slit is applied and the energy intensity value under the condition that the phantom is present and the slit is applied during CT scanning. The phantom simulates the target object during CT scanning. The phantom can be made of materials such as Teflon or water, with a thickness greater than or equal to 3 millimeters to mimic the thickness of a human tissue.

Figure 4:
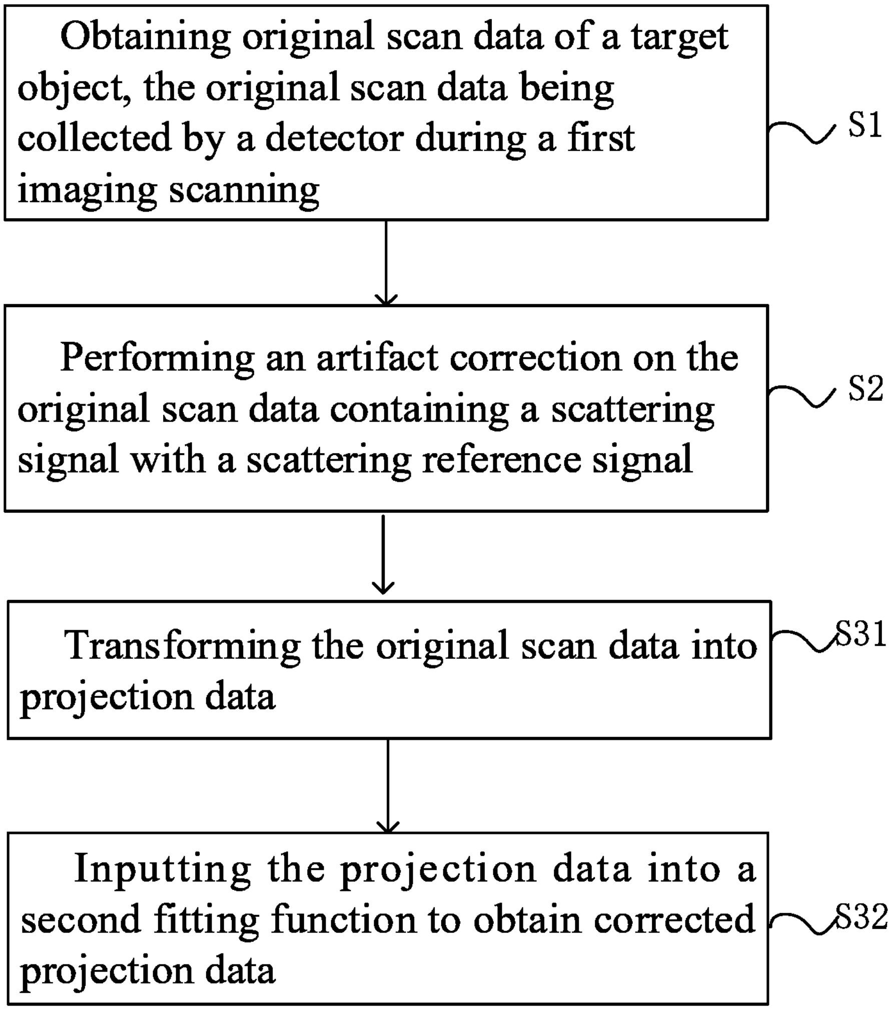
FIG. 4 shows a third flowchart of a method for removing an artifact in an image according to the first embodiment of the present disclosure.

In some embodiments, as shown in FIG. 4, step S3 includes steps S31-S32.

In step S31, the original scan data is transformed into projection data.

Typically, the original scan data obtained from the detector is transformed into projection data using a log (logarithmic) operation. The projection data is arranged in a two-dimensional matrix with detector channels as the horizontal axis and the scan field as the vertical axis, which is essentially an overlapping of curves formed at various points in a medical image.

In step S32, the projection data is input into a second fitting function to obtain corrected projection data, where the coefficients of the second fitting function are determined based on the projection reference signal.

In some embodiments, the second fitting function includes an exponential function or a polynomial function.

In some embodiments, the determination of the coefficients of the second fitting function includes:

obtaining the third detector response (e.g., $A_{spectra}$) under the condition that no phantom is present and the slit is applied, and the fourth detector response (e.g., $I_{spectra}$) under the condition that the phantom is present and the slit is applied;

calculating projection values (e.g., $P_{spectra}$) corresponding to different slit positions using the following equation:

$$P_{spectra}=\log(A_{spectra}/I_{spectra});$$

concatenating the projection values corresponding to different slit positions to form a projection value (e.g., $P_{spectra-all}$) for all pixels.

smoothing the projection value (e.g., $P_{spectra-all}$) to obtain a smoothed projection value (e.g., $P_{spectra-all-smooth}$). The smoothing methods may include, for example, first-order exponential smoothing, second-order exponential smoothing, or third-order exponential smoothing; and performing fitting with the projection value (e.g., $P_{spectra-all}$) as the x-coordinate and the smoothed projection value (e.g., $P_{spectra-all-smooth}$) as the y-coordinate to obtain the coefficients of the second fitting function.

The phantom can be made of materials such as Teflon or water, with a thickness greater than or equal to 3 millimeters to mimic the thickness of a human tissue.

In this embodiment, by using the projection reference signal, an artifact correction is further performed on the projection signal of the original scan data, thereby optimizing the imaging effect of the medical image.

Specific steps of an exemplary method for removing an artifact in an image include steps S41-S45.

In step S41, an air correction is performed on original scan data.

The air correction includes obtaining a set of data as a reference value by performing a scan without any object placed within the scanning range of the scanning device, and then obtaining air-corrected original scan data by subtracting the reference value obtained by scanning only the air from the original scan data.

In step S42, a log operation of the air-corrected original scan data is performed to obtain projection data.

In step S43, the projection data is input into a second fitting function to obtain corrected projection data.

The coefficients of the second fitting function are determined based on the projection reference signal which, in this exemplary embodiment, is obtained by the steps as described above.

In step S44, an inverse log operation of the corrected projection data is performed to obtain projection-corrected original scan data, and a scatter intensity estimation is performed on the projection-corrected original scan data to obtain the original scattering signal. The methods for the scatter intensity estimation include convolution, Monte Carlo algorithms, deep learning, etc. FIG. shows a scattering signal curve obtained after the scatter intensity estimation, where the x-axis represents the channel number of the detector and the y-axis represents the intensity value of the scattering signal.

In step S45, the original scattering signal is input into a first fitting function to obtain a scattering signal.

Figure 5:
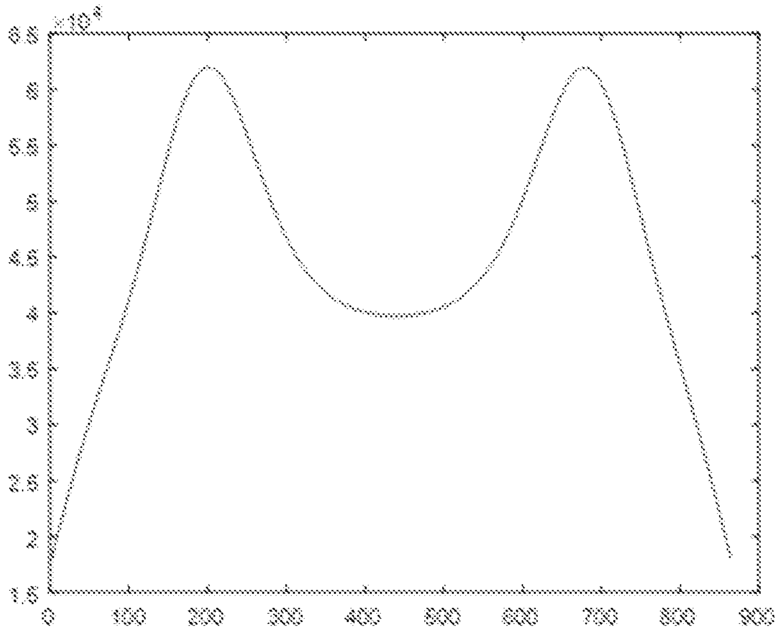
FIG. 5 is a schematic diagram of an intensity of an original scattering signal achieved by the method for removing an artifact in an image according to the first embodiment of the present disclosure.
Figure 6:
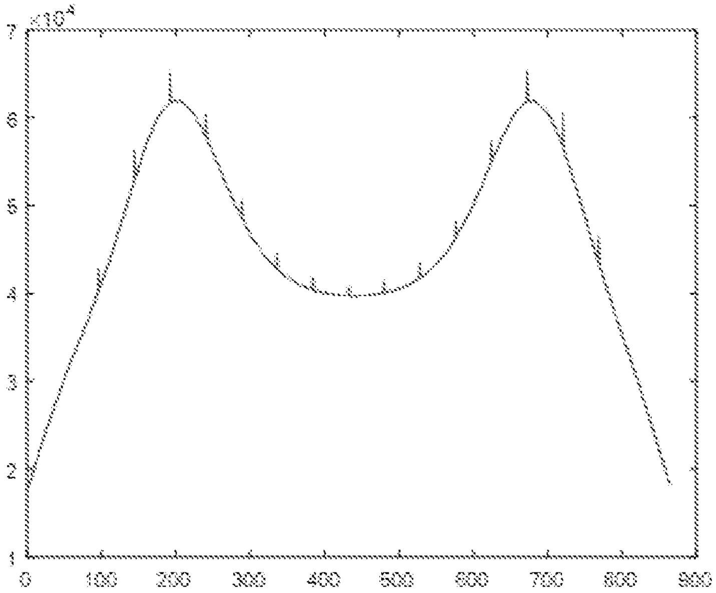
FIG. 6 is a schematic diagram of an intensity of a fitted scattering signal by the method for removing an artifact in an image according to the first embodiment of the present disclosure.

The curve in FIG. 6 represents the original scattering signal (similar to that in FIG. 5), and the prominent peaks on the curve represent the fitted scattering signal. In FIG. 6, the x-axis represents the channel number of the detector and the y-axis represents the intensity value of the scattering signal. FIG. 6 provides a closer approximation to the intensity value of the actual scattering signal, compared to FIG. 5. The prominent peaks on the curve occur because some X-rays may scatter when passing through slits of the detector and reach the edge pixels of the detector (i.e., the dark squares in FIG. 1). This makes the edge pixels receive more X-ray signals than they should, resulting in multiple prominent peaks on the original smooth curve. This is also the reason for the presence of artifacts in the reconstructed image caused by the edge pixels of the detector.

Figure 7:
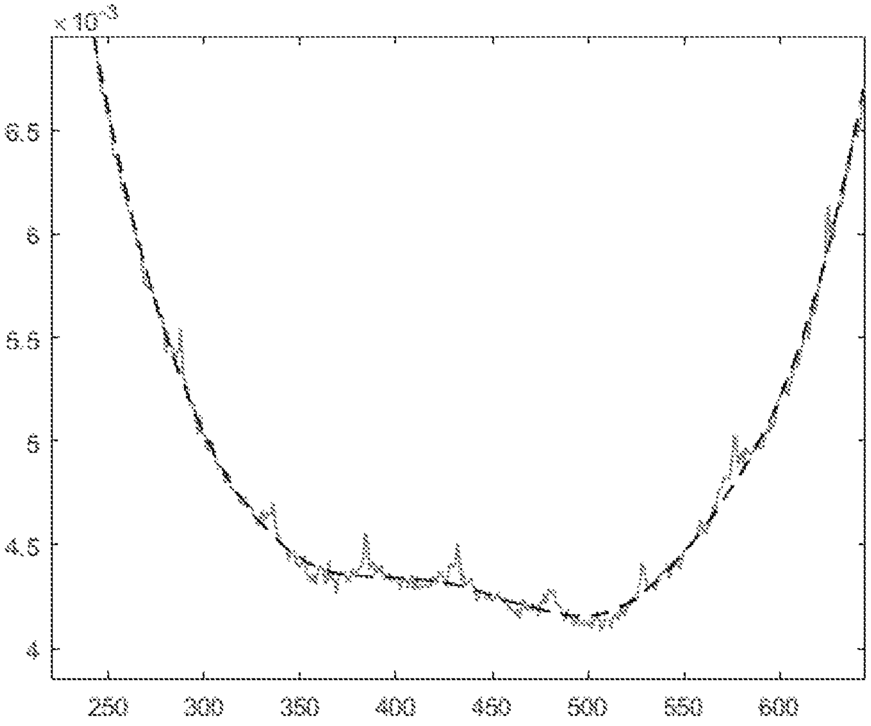
FIG. 7 is a diagram showing a comparison between the intensity of the original scattering signal and the intensity of the fitted scattering signal by the method for removing an artifact in an image according to the first embodiment of the present disclosure.

FIG. 7 shows a comparison between an original scattering signal and the scattering signal obtained by fitting in another test. The x-axis of FIG. 7 represents the channel number of the detector, and the y-axis represents the intensity value of the scattering signal.

In the present embodiment, the coefficients of the first fitting function are determined using the method described above.

In step S46, the scattering signal is removed from the original scan data to perform a further artifact correction.

In step S47, the FBP method is used to reconstruct an artifact-free medical image of the target object based on the original scan data after the above artifact correction.

Embodiment II

Figure 8:
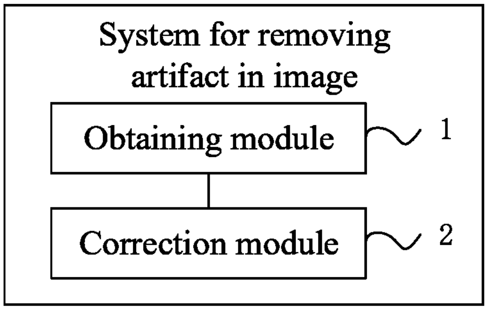
FIG. 8 is a first structural diagram of a system for removing an artifact in an image according to a second embodiment of the present disclosure.

This embodiment provides a system for removing an artifact in an image, as shown in FIG. 8. The system includes:

- an obtaining module 1 configured to obtain original scan data of a target object from a detector during CT scanning;
- a correction module 2 configured to perform an artifact correction on the original scan data containing a scattering signal with a scatter reference signal. The scatter reference signal is obtained based on energy data of the detector obtained under a condition that no slit is applied and energy data of the detector obtained under a condition that a slit is applied during CT scanning.

In some embodiments, the energy data of the detector obtained under the condition that no slit is applied includes an energy intensity value of the detector obtained under a condition that no phantom is present and no slit is applied, and an energy intensity value of the detector obtained under a condition that a phantom is present and no slit is applied.

The energy data of the detector obtained under the condition that the slit is applied includes an energy intensity value of the detector obtained under a condition that no phantom is present and the slit is applied, and an energy intensity value of the detector obtained under a condition that the phantom is present and the slit is applied.

The phantom is used to simulate the target object during CT scanning. The phantom can be made of materials such as Teflon or water, and the thickness of the phantom is greater than or equal to 3 millimeters to mimic the thickness of a human tissue.

Figure 9:
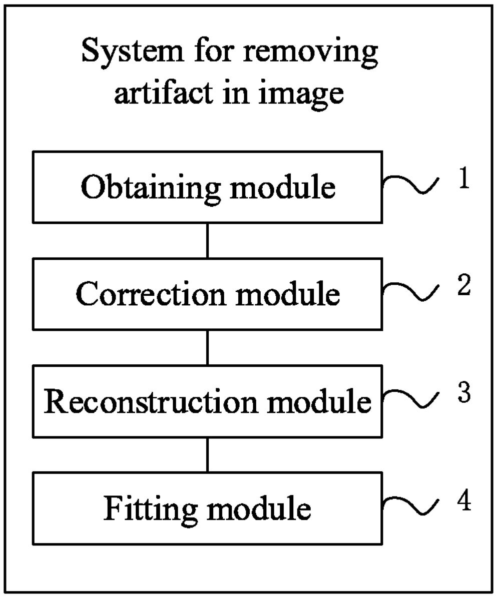
FIG. 9 is a second structural diagram of a system for removing an artifact in an image according to the second embodiment of the present disclosure.

In some embodiments, as shown in FIG. 9, the system further includes:

- a reconstruction module 3 configured to reconstruct an image based on the artifact-corrected original scan data using the FBP method, so as to obtain an artifact-free medical image of the target object.

In the present embodiment, the scatter reference signal obtained based on the energy data of the detector obtained under the condition that no slit is applied and the energy data of the detector obtained under the condition that a slit is applied are used to perform artifact correction on the original scan data containing the scattering signal, thereby removing, for example, ring artifacts in the medical images and achieving better imaging results.

In some embodiments, as shown in FIG. 9, the system further includes a fitting module 4 configured to perform a scatter intensity estimation on the original scan data to obtain an original scattering signal, and input the original scattering signal into a first fitting function to obtain the scattering signal. The coefficients of the first fitting function are determined based on the scatter reference signal. In some embodiments, the coefficients of the first fitting function are obtained based on the method described above.

The correction module 2 is further configured to remove the scattering signal from the original scan data to obtain the artifact-corrected original scan data.

In this embodiment, the scattering signal in the original scan data is removed through the scatter intensity estimation and the fitting algorithm. This realizes artifact correction on the original scan data by removing the scatter signal from the original scan data, and simplifies the correction of artifacts, which reduces maintenance costs and improves imaging quality.

In some embodiments, the correction module 2 is further configured to perform an artifact correction on the original scan data containing a projection signal with a projection reference signal.

The projection reference signal is obtained based on the energy intensity value of the detector obtained under the condition that no phantom is present and a slit is applied and the energy intensity value of the detector obtained under the condition that the phantom is present and the slit is applied during CT scanning. The phantom simulates the target object during CT scanning. The phantom can be made of materials such as Teflon or water, with a thickness greater than or equal to 3 millimeters to mimic the thickness of a human tissue.

In some embodiments, the fitting module 4 is further configured to transform the original scan data into projection data, and input the projection data into a second fitting function to obtain corrected projection data. The coefficients of the second fitting function are determined based on the projection reference signal.

In this embodiment, by using the projection reference signal, an artifact correction is further performed on the projection signal of the original scan data, thereby optimizing the imaging effect of the medical image.

Embodiment III

Figure 12:
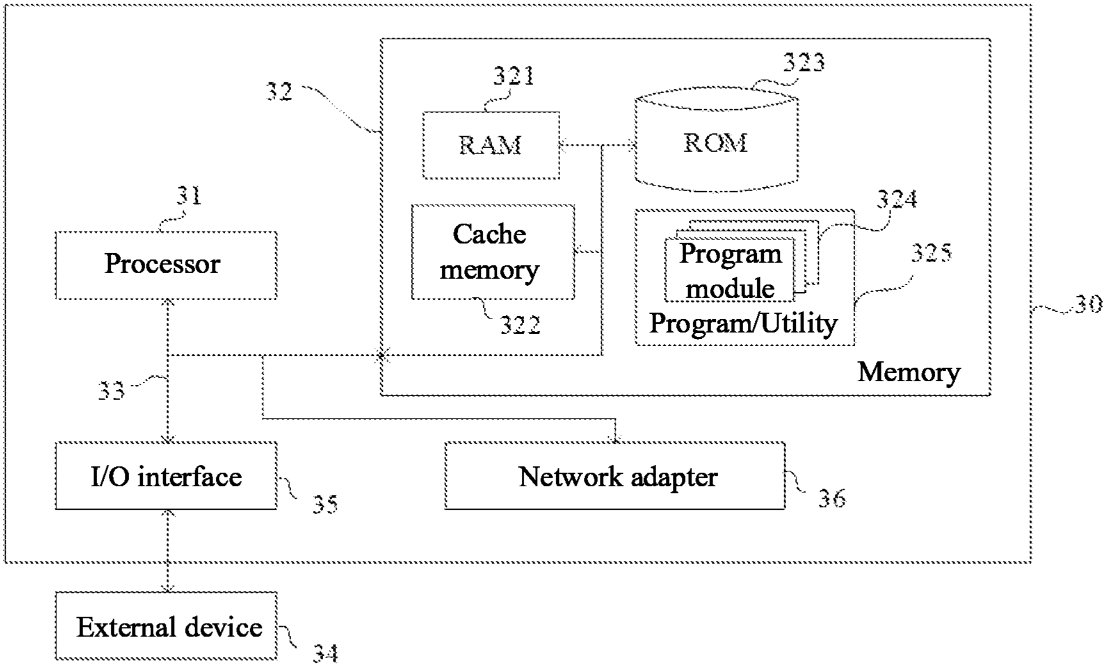
FIG. 12 is a schematic structural diagram of an electronic device according to a third embodiment of the present disclosure.

This embodiment provides an electronic device. FIG. 12 is a schematic diagram of the modules of the electronic device 30. The electronic device includes a memory, a processor, and a computer program stored in the memory and executable by the processor to implement the method for removing an artifact in an image as described in Embodiment I. The electronic device 30 shown in FIG. 12 is just exemplary and is not intended to constitute any limitations on the functionality and scope of use of embodiments of the disclosure.

As shown in FIG. 12, the electronic device 30 can be a general computing device, such as a server. The components of the electronic device 30 may include, but are not limited to, at least one processor 31, at least one memory 32, and a bus 33 that connects different system components (including memory 32 and processor 31).

The bus 33 includes a data bus, an address bus, and a control bus.

The memory 32 may include a transitory memory, such as a random-access memory (RAM) 321 and/or a cache memory 322, and may further include a non-transitory memory such as a read-only memory (ROM) 323.

The memory 32 may also include a program/utility 325 including a set (at least one) of program modules 324. These program modules 324 may include, but are not limited to, an operating system, one or more application programs, other program modules, and program data, one or a combination of which can implement a network environment.

The processor 31 performs various functional applications and data processing by running the computer program stored in the memory 32, such as a method for removing an artifact in an image as described in Embodiment I.

The electronic device 30 can also communicate with one or more external devices 34 (such as a keyboard, pointing device, etc.). This communication can be done through an input/output (I/O) interface 35. Additionally, the electronic device 30 may communicate with one or more networks (such as a local area network (LAN), wide area network (WAN), and/or public network such as the internet) via a network adapter 36. As shown in FIG. 12, the network adapter 36 communicates with other modules of the electronic device 30 via the bus 33. It should be understood that although not shown in the figure, other hardware and/or software modules can be used in conjunction with the electronic device 30, including but not limited to microcode, device drivers, redundant processors, external disk drive arrays, RAID (redundant array of independent disks) systems, tape drives, and data backup storage systems.

It should be noted that although several units/modules or subunits/modules of the electronic device have been described in detail above, this division is merely exemplary and not mandatory. In fact, according to embodiments of the disclosure, the features and functions of two or more units/modules described above can be implemented in a single unit/module. Vice versa, the features and functions of one unit/module described above can be implemented by multiple units/modules.

Embodiment IV

This embodiment provides a non-transitory computer-readable storage medium on which a computer program is stored. When the program is executed by a processor, a method for removing an artifact in an image as described in Embodiment I is performed.

The non-transitory computer-readable storage medium may include, but is not limited to, portable disks, hard drives, read-only memory (ROM), erasable programmable read-only memory (EPROM), optical memory devices, magnetic storage devices, or any suitable combination thereof.

In possible embodiments, the disclosure can also be implemented in the form of a program product that includes program codes. When the program product is run on a terminal device, the program codes enable the terminal device to perform a method for removing an artifact in an image as described in the Embodiment I.

The program codes for implementing the disclosure can be written in one or more programming languages and can include a combination of programming languages. The program codes can be executed entirely on the user device, partially on the user device, as a stand-alone software package, partially on the user device and partially on a remote device, or entirely on the remote device.

Although specific embodiments of the disclosure have been disclosed above, it should be understood that these are merely examples and the scope of the disclosure is defined by the accompanying claims. Those skilled in the art may make various changes or modifications to these embodiments without departing from the principles and essence of the disclosure, and such changes and modifications are within the scope of protection of the disclosure.

What is claimed is:

1. A method for removing an artifact in an image, comprising:

obtaining original scan data of a target object, the original scan data being collected by a detector during a first imaging scanning, the original scan data containing a scattering signal;

performing an artifact correction on the original scan data with a scattering reference signal, wherein the scattering reference signal is obtained based on energy data of the detector obtained under a condition that no slit is applied and energy data of the detector obtained under a condition that a slit is applied during a second imaging scanning;

performing a scatter intensity estimation on the original scan data to obtain an original scattering signal; and inputting the original scattering signal into a first fitting function to obtain the scattering signal;

wherein the scattering reference signal comprises a first detector response under a condition that no phantom is present and no slit is applied, a second detector response under a condition that a phantom is present and no slit is applied, a third detector response under a condition that no phantom is present and the slit is applied, and a fourth detector response under a condition that the phantom is present and the slit is applied, and coefficients of the first fitting function are determined based on the first detector response, the second detector response, the third detector response, and the fourth detector response.

2. The method according to claim 1, wherein the energy data of the detector obtained under the condition that no slit is applied comprises an energy intensity value of the detector obtained under a condition that no phantom is present and no slit is applied, and an energy intensity value of the detector obtained under a condition that a phantom is present and no slit is applied;

the energy data of the detector obtained under the condition that the slit is applied comprises an energy intensity value of the detector obtained under the condition that no phantom is present and the slit is applied, and an energy intensity value of the detector obtained under a condition that the phantom is present and the slit is applied;

the phantom is configured to simulate the target object during the second imaging scanning; and the first imaging scanning and the second imaging scanning are each a CT scanning, a PET scanning, a PET-CT scanning, or an enhancement CT scanning.

3. The method according to claim 2, wherein the performing the artifact correction on the original scan data with the scattering reference signal further comprises:

removing the scattering signal from the original scan data to obtain artifact-corrected original scan data; and generating an image based on the artifact-corrected original scan data.

4. The method according to claim 1, wherein the determining the coefficients of the first fitting function based on the first detector response, the second detector response, the third detector response, and the fourth detector response comprises:

calculating normalized intensities of the fourth detector responses corresponding to different slit positions, the normalized intensity of the fourth detector response being equal to a ratio of the fourth detector response to the third detector response;

concatenating the normalized intensities corresponding to different slit positions to form a normalized intensity for all pixels of the detector;

calculating a normalized intensity of the second detector response, the normalized intensity of the second detector response being equal to a ratio of the second detector response to the first detector response;

obtaining a scatter intensity by removing the normalized intensity for all pixels of the detector from the normalized intensity of the second detector response;

smoothing the scatter intensity to obtain a smoothed scatter intensity; and performing fitting with the smoothed scatter intensity as the x-coordinate and the scatter intensity as the y-coordinate to obtain the coefficients of the first fitting function.

5. The method according to claim 3, wherein the performing the scatter intensity estimation on the original scan data to obtain the original scattering signal comprises:

analyzing the original scan data using an algorithm, model, or neural network to obtain the original scattering signal.

6. The method according to claim 1, further comprising:

performing an artifact correction on the original scan data containing a projection signal with a projection reference signal to obtain projection-corrected original scan data, wherein the projection reference signal is obtained based on an energy intensity value of the detector obtained under a condition that no phantom is present and the slit is applied and an energy intensity value of the detector obtained under a condition that the phantom is present and the slit is applied during CT scanning.

7. The method according to claim 6, wherein the performing the artifact correction on the original scan data containing the projection signal with the projection reference signal comprises:

transforming the original scan data into projection data; and inputting the projection data into a second fitting function to obtain the corrected projection data, wherein coefficients of the second fitting function are determined based on the projection reference signal.

8. The method according to claim 7, wherein the determination of the coefficients of the second fitting function comprises:

obtaining the projection reference signal comprising a third detector response under a condition that no phantom is present and a slit is applied, and a fourth detector response under a condition that the phantom is present and the slit is applied; and determining the coefficients of the second fitting function based on the third detector response and the fourth detector response.

9. The method according to claim 8, wherein the determining the coefficients of the second fitting function based on the third detector response and the fourth detector response comprises:

calculating projection values corresponding to different slit positions by performing a log operation on a ratio of the third detector response to the fourth detector response;

concatenating the projection values corresponding to the different slit positions to form a projection value for all pixels of the detector;

smoothing the projection value for all pixels of the detector to obtain a smoothed projection value; and performing fitting with the smoothed projection value as the y-coordinate and the projection value for all pixels of the detector as the x-coordinate to obtain the coefficients of the second fitting function.

10. The method according to claim 6, wherein the performing the artifact correction on the original scan data with the scattering reference signal comprises:

performing the artifact correction on the projection-corrected original scan data with the scattering reference signal.

11. The method according to claim 6, wherein before performing the artifact correction on the original scan data containing the projection signal with the projection reference signal, the method further comprises:

performing an air correction on the original scan data to obtain air-corrected original scan data.

12. The method according to claim 6, further comprising:

analyzing the original scan data using an algorithm, model, or neural network to obtain original scattering signal;

removing the original scattering signal from the projection-corrected original scan data to obtain artifact-corrected original scan data; and generating an image based on the artifact-corrected original scan data.

13. The method according to claim 6, wherein the energy data of the detector obtained under the condition that the slit is applied comprises energy data generated by the detector when a baffle with the slit is placed between the detector and a light source, and the energy data of the detector obtained under the condition that no slit is applied comprises energy data generated by the detector when the baffle with the slit is removed.

14. An electronic device, comprising a memory, a processor, and a computer program stored in the memory and executable by the processor, wherein the processor, when executing the computer program, performs a method for removing an artifact in an image, the method comprising:

obtaining original scan data of a target object, the original scan data being collected by a detector during a first imaging scanning, the original scan data containing a scattering signal;

performing an artifact correction on the original scan data with a scattering reference signal, wherein the scattering reference signal is obtained based on energy data of the detector obtained under a condition that no slit is applied and energy data of the detector obtained under a condition that a slit is applied during a second imaging scanning;

performing a scatter intensity estimation on the original scan data to obtain an original scattering signal; and inputting the original scattering signal into a first fitting function to obtain the scattering signal;

wherein the scattering reference signal comprises a first detector response under a condition that no phantom is present and no slit is applied, a second detector response under a condition that a phantom is present and no slit is applied, a third detector response under a condition that no phantom is present and the slit is applied, and a fourth detector response under a condition that the phantom is present and the slit is applied, and coefficients of the first fitting function are determined based on the first detector response, the second detector response, the third detector response, and the fourth detector response.

15. The electronic device according to claim 14, wherein the energy data of the detector obtained under the condition that no slit is applied comprises an energy intensity value of the detector obtained under the condition that no phantom is present and no slit is applied, and an energy intensity value of the detector obtained under the condition that a phantom is present and no slit is applied;

the energy data of the detector obtained under the condition that the slit is applied comprises an energy intensity value of the detector obtained under the condition that no phantom is present and the slit is applied, and an energy intensity value of the detector obtained under the condition that the phantom is present and the slit is applied;

the phantom is configured to simulate the target object during the second imaging scanning; and the first imaging scanning and the second imaging scanning are each a CT scanning, a PET scanning, a PET-CT scanning, or an enhancement CT scanning.

16. The electronic device according to claim 15, wherein the performing the artifact correction on the original scan data with the scattering reference signal comprises:

performing a scatter intensity estimation on original scan data to obtain an original scattering signal;

inputting the original scattering signal into a first fitting function to obtain the scattering signal, wherein coefficients of the first fitting function are determined based on the scattering reference signal;

removing the scattering signal from the original scan data to obtain artifact-corrected original scan data; and generating an image based on the artifact-corrected original scan data.

17. The electronic device according to claim 16, wherein the determination of the coefficients of the first fitting function comprises:

obtaining the scattering reference signal comprising a first detector response under the condition that no phantom is present and no slit is applied, a second detector response under the condition that the phantom is present and no slit is applied, a third detector response under the condition that no phantom is present and the slit is applied, and a fourth detector response under the condition that the phantom is present and the slit is applied;

calculating normalized intensities of the fourth detector responses corresponding to different slit positions, the normalized intensity of the fourth detector response being equal to a ratio of the fourth detector response to the third detector response;

concatenating the normalized intensities corresponding to different slit positions to form a normalized intensity for all pixels of the detector;

calculating a normalized intensity of the second detector response, the normalized intensity of the second detector response being equal to a ratio of the second detector response to the first detector response;

obtaining a scatter intensity by removing the normalized intensity for all pixels of the detector from the normalized intensity of the second detector response;

smoothing the scatter intensity to obtain a smoothed scatter intensity; and performing fitting with the smoothed scatter intensity as the x-coordinate and the scatter intensity as the y-coordinate to obtain the coefficients of the first fitting function.

18. A method for removing an artifact in an image, comprising:

obtaining original scan data of a target object, the original scan data being collected by a detector during a first imaging scanning, the original scan data containing a projection reference signal; and performing an artifact correction on the original scan data with a projection reference signal to obtain projection-corrected original scan data, wherein the projection reference signal is obtained based on an energy intensity value of the detector obtained under a condition that no phantom is present and the slit is applied and an energy intensity value of the detector obtained under a condition that the phantom is present and the slit is applied during a second imaging scanning, wherein performing the artifact correction comprises:

transforming the original scan data into projection data; and inputting the projection data into a second fitting function to obtain corrected projection data, wherein coefficients of the second fitting function are determined by:

calculating projection values corresponding to different slit positions by performing a log operation on a ratio of a third detector response under the condition that no phantom is present and the slit is applied to a fourth detector response under the condition that the phantom is present and the slit is applied;

concatenating the projection values corresponding to the different slit positions to form a projection value for all pixels of the detector;

smoothing the projection value for all pixels of the detector to obtain a smoothed projection value; and performing fitting with the smoothed projection value as a y-coordinate and the projection value for all pixels of the detector as an x-coordinate to obtain the coefficients of the second fitting function.

19. A non-transitory computer-readable storage medium comprising a computer program stored therein, wherein the computer program, when executed by a processor, causes the processor to perform a method for removing an artifact in an image according to claim 1.

* * * * *